United States Patent [19]

DiBenedetto et al.

[11] Patent Number: 4,602,644
[45] Date of Patent: Jul. 29, 1986

[54] PHYSIOLOGICAL DETECTOR AND MONITOR

[75] Inventors: John P. DiBenedetto, Norwood; Jerome L. Krasner, Ashland, both of Mass.

[73] Assignee: Plasmedics, Inc., Englewood, Colo.

[21] Appl. No.: 409,306

[22] Filed: Aug. 18, 1982

[51] Int. Cl.[4] .............................................. A61B 5/08
[52] U.S. Cl. .............................. 128/725; 128/207.18; 128/721; 128/671
[58] Field of Search ................... 128/207.18, 716, 718, 128/720, 721, 722, 724, 725, 671, 689

[56] References Cited

U.S. PATENT DOCUMENTS

| | | | |
|---|---|---|---|
| 3,566,862 | 3/1971 | Schuh et al. | 128/207.18 |
| 3,884,219 | 5/1975 | Richardson et al. | 128/724 |
| 4,306,567 | 12/1981 | Krasner | 128/721 |

Primary Examiner—Edward M. Coven
Attorney, Agent, or Firm—Schiller & Pandiscio

[57] ABSTRACT

An improved detector and monitor for use with the detector are disclosed for detecting and monitoring a physiological rhythmic signal. When detecting respiration the detector or the monitor is adapted to distinguish between airflow response to inhalation and airflow responsive to exhalation.

60 Claims, 16 Drawing Figures

FIG. 4
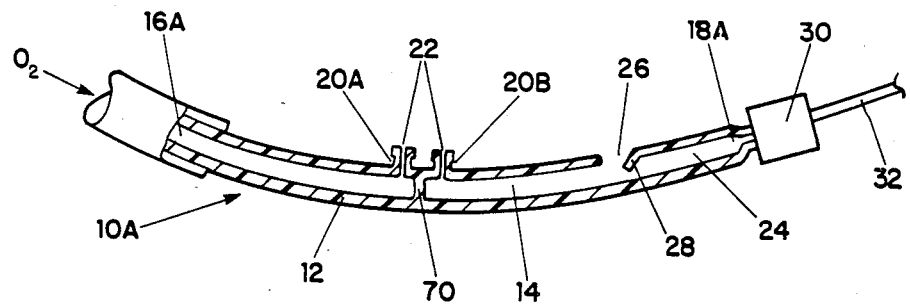
FIG. 5
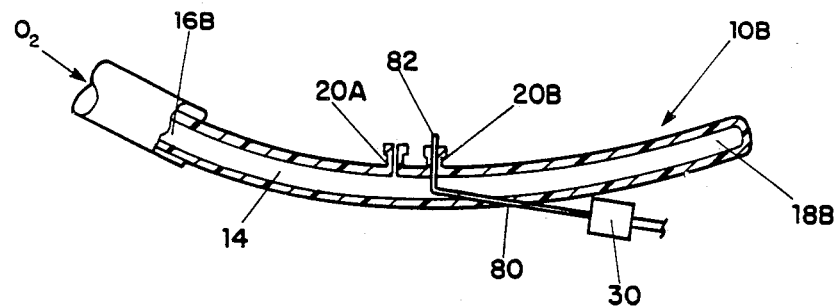
FIG. 6
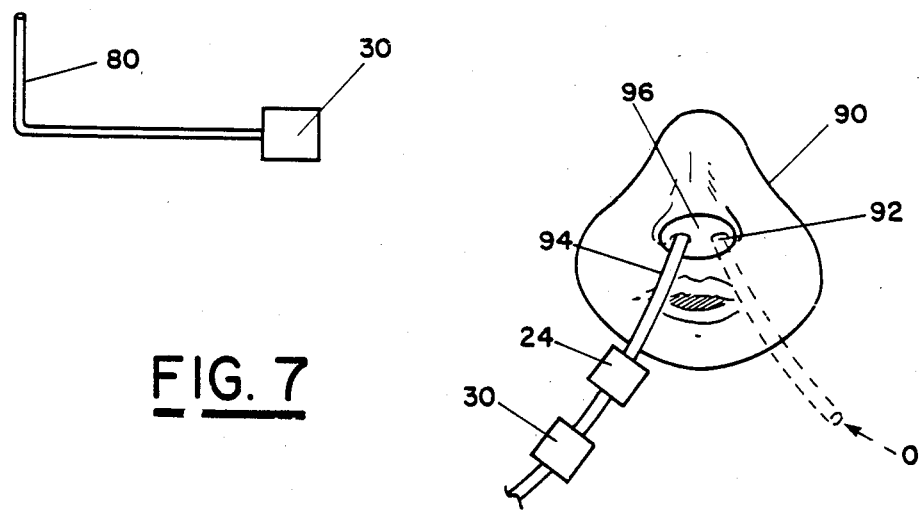
FIG. 7

FIG. 8
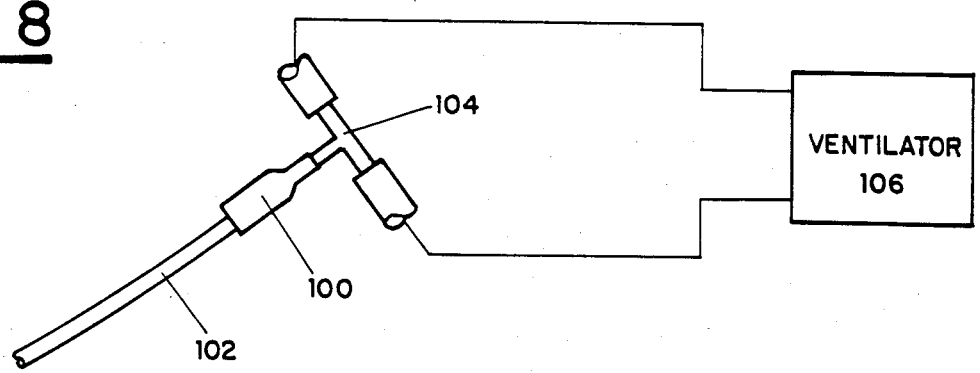
FIG. 9
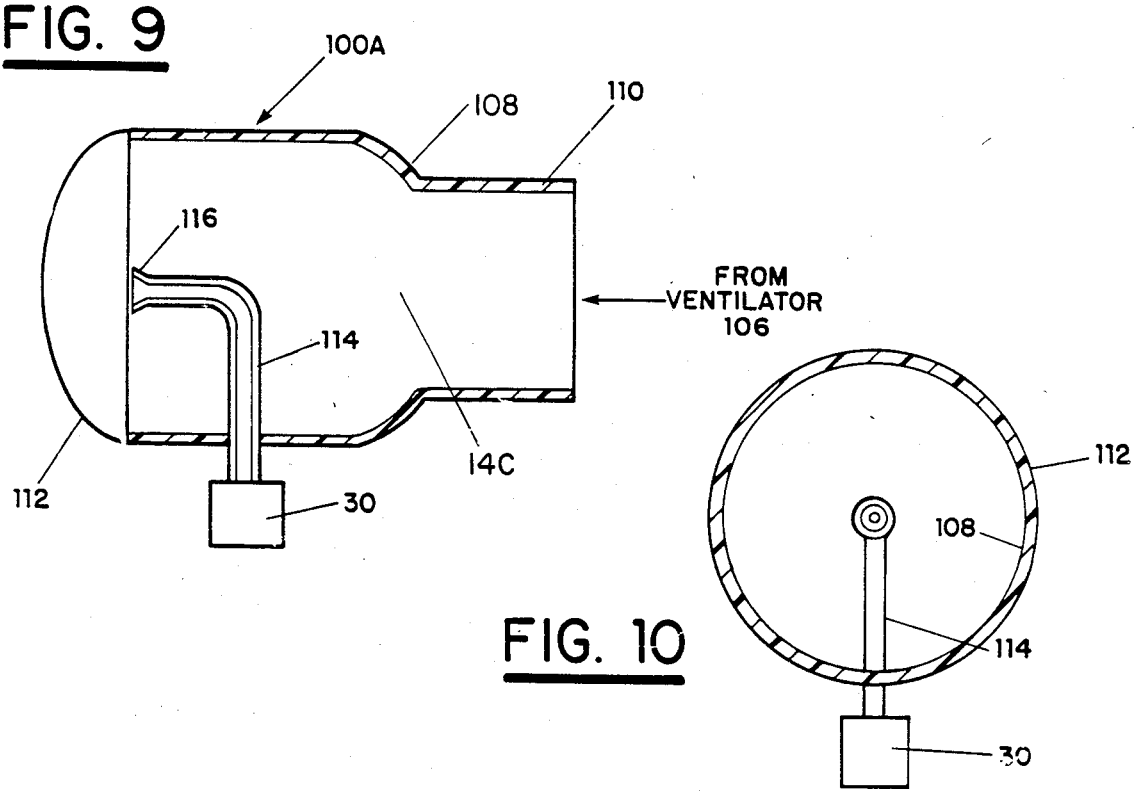
FIG. 10
FIG. 11
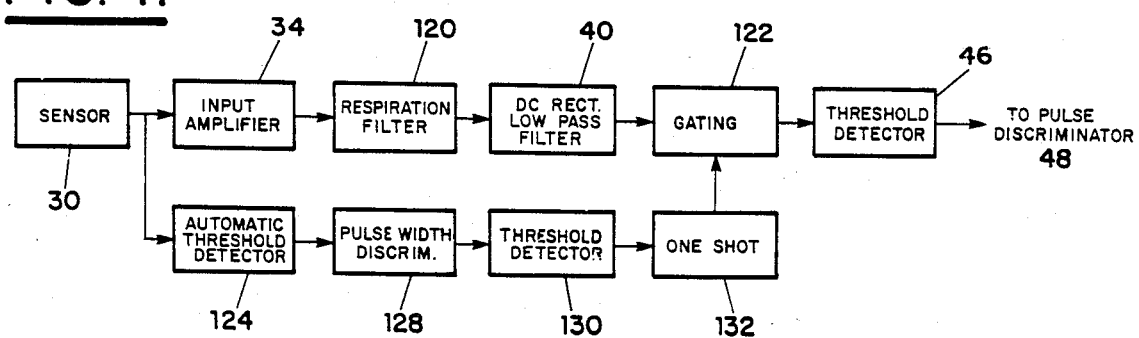

PHYSIOLOGICAL DETECTOR AND MONITOR

The present invention relates generally to the acquisition of certain physiological signals and more particularly to the detection and monitoring of respiration.

U.S. Pat. No. 4,306,567, issued Dec. 22, 1981 to Dr. Jerome L. Krasner, discloses an improved apparatus (hereinafter referred to for convenience as the "Krasner Monitor") for detecting and monitoring certain physiological signals such as heart rate and respiration. The device described is particularly useful for monitoring humans, such as newborns, so that apnea, or the cessation of breathing, can be easily detected. As described in the patent, the Krasner Monitor is an improvement over other monitors of both the (A) contacting type (such as those utilizing (1) strain gage sensors placed around the chest so as to measure chest expansion, (2) impedance pnuemographs in which a high frequency signal is created between thoracically-mounted electrodes and changes in chest impedance are measured, (3) magnetometers for detecting the distance between two electrodes, or (4) thermistors for placement in the nasal orifices) and (B) noncontacting type (such as those employing (1) mattresses, or (2) ultrasonic sensors to detect motion via phase change). In particular, as described in U.S. Pat. No. 4,306,567, the Krasner Monitor detects within a relatively narrow band of frequencies (characteristic of and unique with respect to the physiological rhythmic function of the body being monitored), the pressure waves generated by the physiological function of the body. The Krasner Monitor generates an electrical signal representative of the acoustical energy within the frequency band detected from the subject. The electrical signal is demodulated and filtered so that the portions of the filtered, demodulated signal representative of acoustical energy detected from the subject and attributed to the physiological function encompasses a band of frequencies which includes the frequency at which the optimum or near optimum signal-to-noise ratio occurs in order to distinguish between those portions of the filtered demodulated signal generated in response to the rhythmic function and those in response to motion artifacts.

The Krasner Monitor, as described in U.S. Pat. No. 4,306,567, thus substantially isolates the natural frequency signal associated with the body function at which the signal-to-noise ratio is at a maximum or near maximum. While this principle has been proven clinically, there may be some variation of this natural frequency from person to person (e.g., the natural frequency of elderly patients may differ from that of newborns), and may vary from location to location (e.g., hospital use may vary from home use). Further, the fundamental frequency characteristics of inhalation and exhalation are very similar so that it may be difficult to discern the difference between the two and thus to monitor the respiration rate.

It is an object of the present invention, therefore, to generate an acoustic signal in response to the body function within a very precisely tuned narrow frequency band so that the signal-to-noise ratio can be further enhanced.

Another object of the present invention is to provide a device useful with the Krasner Monitor for generating a finely tuned acoustic signal in response to the physiological function being monitored, the signal having a fundamental frequency higher than the dominant acoustic frequencies normally present in the physiological function so as to enhance the signal-to-noise ratio of the detected signal.

And another object of the present invention is to provide a detector useful with the Krasner Monitor, the detector being relatively inexpensive so that it is disposable after use by a patient.

Yet another object of the present invention is to provide an improved device for detecting and monitoring respiration.

Still another object of the present invention is to provide a system, adapted for use with the Krasner Monitor, for generating only in response to either inhalation or exhalation, a finely tuned acoustical signal within a band of frequencies at which the signal-to-noise ratio is optimum or near optimum.

And yet another object of the present invention is to provide an improved attachment for use with the Krasner Monitor for detecting airflow either to or from a living body and which can be easily adapted for use with respiratory instruments, such as endotracheal and tracheostomy tubes.

And still another object of the present invention is to provide an improved system for monitoring respiration of a subject wherein the system is responsive to only either inhalation or exhalation of the subject so as to further enhance the signal-to-noise ratio.

And yet another object is to provide an improved device for monitoring physiological signals such as respiration by using the signal content at one frequency to monitor the signal content at another frequency so as to improve the signal-to-noise ratio.

These and other objects are achieved by an improved device for sensing a physiological function, such as respiration, in a living body, as well as an improved system for monitoring such physiological function.

In accordance with one aspect of the present invention, a system is provided for monitoring over a relatively long period of time the rate of a physiological rhythmic function of a subject. The system comprises detection means for detecting acoustical energy generated in response to the physiological rhythmic function of said subject. Signal generating means responsive to the detected acoustical energy is provided so as to generate a first electrical signal containing signal information within at least two bands of frequencies and representative of said acoustical energy generated in response to the physiological function of said subject. The system also comprises means responsive to the signal information in one of said bands for generating a second electrical signal in response to preselected portions of said signal information in the other of said bands; and means for processing said second electrical signal so as to produce a third signal representative of the rate of said physiological rhythmic function.

In accordance with another aspect of the present invention, when detecting respiration the signal generated by the detector responsively to respiration is such that inhalation is more easily distinguishable from exhalation.

In accordance with another aspect of the present invention, a device for use in detecting respiration of a living body comprises means adapted to be positioned relative to the respiratory airway of the living body so as to define an air passageway for providing air flow in a first direction responsively to inhalation by the body, and a second direction responsively to exhalation by the body. Acoustic signal generating means are disposed relative to the passageway for generating responsively to air flow in only a selected one of the directions, an acoustic signal having a fundamental frequency higher than the dominant acoustic frequencies normally present in the respiration function of the living body. Means are disposed relative to the acoustic signal generating means for detecting the acoustical signal and for generating an electrical signal representative of said acoustic signal. The device of the present invention when used with a Krasner-like Monitor provides an improved apparatus for detecting and monitoring respiration by enhancing the signal-to-noise ratio within the preselected band of frequencies by monitoring only either inhalation or exhalation, at frequencies above much of the noise normally present.

Other objects of the invention will in part be obvious and will in part appear hereinafter. The invention accordingly comprises the apparatus possessing the construction, combination of elements, and arrangement of parts which are exemplified in the following detailed disclosure and the scope of the application of which will be indicated in the claims.

For a further understanding of the nature and objects of the present invention, reference should be had to the following detailed description taken in connection with the accompanying drawings, wherein:

FIG. 4 is a cross-sectional view along the center axis of the air passageway of a second embodiment of a nasal cannula incorporating the present invention;

FIG. 5 shows a cross-sectional view along the center axis of the air passageway of a third embodiment of a nasal cannula incorporating the present invention;

FIG. 6 is an enlarged perspective view of the insert prongs used in the FIG. 5 embodiment; application of which will be indicated in the claims.

FIG. 7 shows a frontal view of an oxygen mask incorporating the principles of the present invention;

FIG. 8 shows a perspective view of an acoustic endotracheal tube adapter incorporating the present invention and used with a standard endotracheal tube and a ventilator;

FIG. 9 is an enlarged perspective axial view of a first embodiment of the acoustic endotracheal tube adapter incorporating the present invention and used in FIG. 8;

FIG. 10 is a cross-sectional view taken along line 10—10 in FIG. 9;

FIG. 11 illustrates a block diagram of the Krasner Monitor which has been modified to incorporate the present invention so as to operate with the nasal cannula shown in FIGS. 9 and 10;

Figure 1:
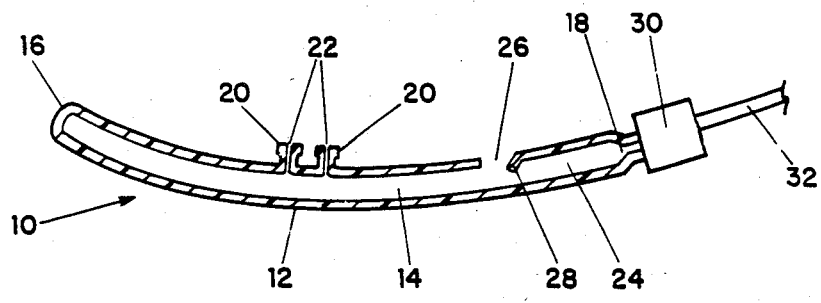
FIG. 1 shows a cross-sectional view along the center axis of the air passageway of a first embodiment of a detector in the form of a nasal cannula modified to incorporate the present invention.

Referring to the drawings wherein the same numerals refer to like parts, the devices shown each define a passageway which can be "connected" to the respiratory airway (either anatomically by insertion or near insertion of the device, into the body such as each of the nasal cannulas shown in FIGS. 1, 2, 4, and 5, or alternatively into a mask worn by the user such as shown in FIG. 9, or mechanically by connecting the device, such as each of the adapters shown generally in FIG. 10 and in greater detail in FIGS. 11–13 and 14–15, to breathing assistance apparatus, such as a ventilator). Each device, when so connected, produces during breathing a unique acoustical signature which enhances the signal-to-noise ratio for processing by, for example, the Krasner Monitor. In addition, these devices are direction specific such that inhalation or exhalation can be readily and specifically distinguished and identified.

Figure 2:
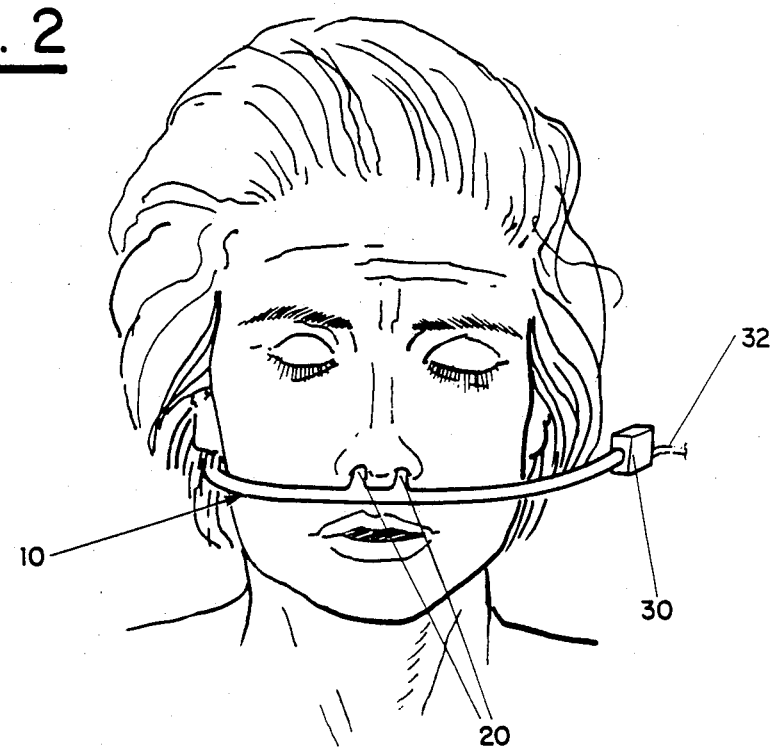
FIG. 2 shows the embodiment of FIG. 1 in use.

Referring to FIG. 1, the nasal cannula 10 includes a hollow tubular body 12 having an air passageway 14, a closed end 16 and a closed end 18. Two nostril inserts 20 radially extend from the tubular body between the ends 16 and 18. Inserts 20 are open at their outer extremeties at 22 and communicate with the air passageway 14 so that they can be inserted in or placed near the nostrils of the user. In accordance with one aspect of the present invention, the cannula is provided with means for generating an acoustic signal within a preselected, relatively narrow band of frequencies and means for detecting this acoustic signal. In the FIG. 1 embodiment the means for generating the acoustic signal is in the form of an acoustic resonant cavity 24 (sometimes referred to as a whistle), created by at least one aperture 26 provided between the nostril inserts 20 and the closed end 18, and a partial obstruction 28 partially extending into passageway 14 so as to create eddies in the resonant cavity 24 from the substantially laminar flow of air flowing in the passageway 14 from the inserts 20 preferably in response to exhalation by the user. The partial obstruction 28 can take several different forms, as are known in whistle art. As shown in FIG. 1, the obstruction 28 is merely a lip extending from the edge of the aperture 26 nearest to the closed end 18 and terminating in a thin edge. When air is forced through the nostril inserts 20, the flow of air is substantially laminar in the narrow passageway until it reaches the narrowing created by the obstruction 28, wherein an instability or eddies are created in the closed ended resonant cavity between the obstruction 28 and the closed end 18. This instability produces in the resonant cavity a narrow band tone or signal (within a bandwidth of frequencies) the frequency of which is a function of the flow rate. Generally, as the flow rate increases the tone frequency increases. The whistle is designed to produce tones for extremely low airflow rates, and with typical airflow rates associated with respiration the range of possible tones is contained within a limited range of frequencies. In most applications the amplitude of sound is below the auditory thresholds for humans so that the user will not hear the tone. The means for detecting the acoustic signal comprises an acoustic signal pressure detector 30, such as a microphone for detecting the acoustic signal generated in the resonant cavity. The detector 30 preferably forms the closed end 18. As will be evident hereinafter, the detector 30 provides an electrical signal representative of the acoustical signal generated in the cavity. As shown in FIG. 2, the nasal cannula 10 can be worn by a spontaneously breathing person by placing the cannala in or near the nostrils of the user.

Figure 3:
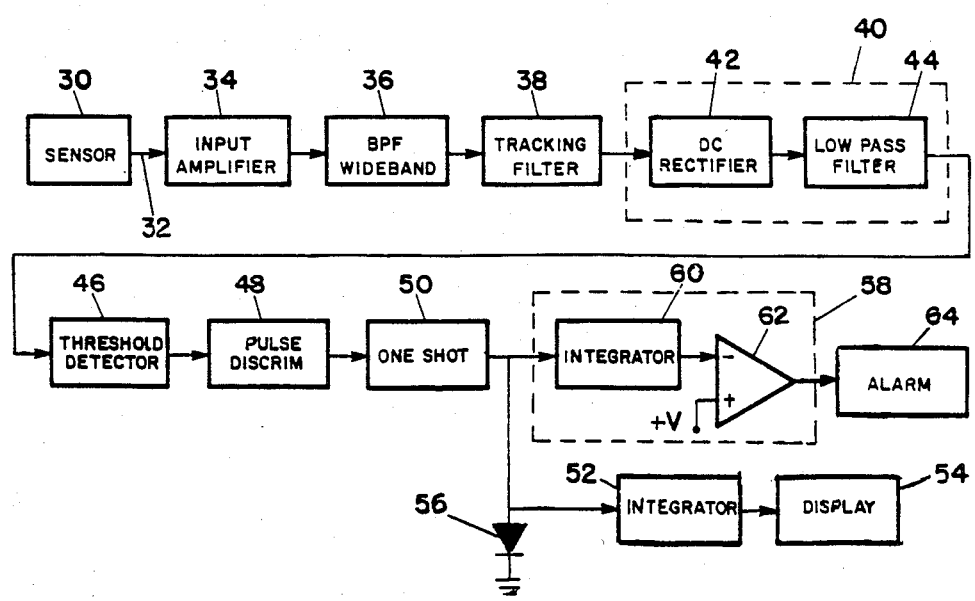
FIG. 3 illustrates a block diagram of the Krasner Monitor which has been modified to incorporate the present invention so as to operate with the nasal cannula shown in FIG. 1.

As shown in FIG. 3, detector 30 is preferably electrically connected (through leads 32 shown in FIG. 2) to apparatus constructed in accordance with the teachings of U.S Pat. No. 4,306,567, and modified in accordance with the present invention. More particularly, the detector 30 is connected to input amplifier 34 for amplifying and shaping the signals detected. Amplifier 34 is connected to the input of a wideband band pass filter 36. The latter is designed to pass those spectral portions of the signal detected which include the range of tones generated in the resonant cavity while at the same time blocking those spectral portions of the signal where most noise (generated in the environment as well as by motion artifacts) is present. The filter 36 is preferably of the active type so as to provide gain depending upon the relative strength of the signal. Each filter may, for example, be a state variable filter with a center frequency at the frequency generated by the detector 30 in response to the lowest velocity air flow detected. A typical center frequency is between about 800 to 1200 Hz with the range of tones being generated by the detector being between about 800–1200 Hz at the low end and anywhere from about 1200–4000 Hz at the high end. The filter should have a very steep skirt at its low frequency cut off (e.g., a slope of about 48 dB/octave), and roll off at about −12 dB/octave so that it passes portions of the spectral energy outside the resonant frequency of respiration as well as most of the environmental noise and noise associated with motion artifacts, but includes the spectral energy within the range of tones generated by the detector. The output of filter 36 is connected to means 38 for locking onto the frequency of the tone being generated by the detector. The means 38 may be any of various devices known for locking onto a narrow band signal, such as a tracking filter, or alternatively, a phase lock loop circuit, both of which are well known to those skilled in the art. In both instances the means 38 locks onto the signal, and holds the signal even though the frequency of the signal typically shifts in a continous fashion from its lower frequency, e.g., 800–1200 Hz, to its upper frequency, e.g., 1200 Hz–4000 Hz., during exhalation.

The remainder of the system is the same as those corresponding elements described in U.S. Pat. No. 4,306,567. Specifically, the output of means 38 is connected to means 40 for demodulating the output of the signal so as to provide a signal representative of the envelope of the signal output of the means 38. Means 40 is shown as including a D.C. rectifier 42, preferably a full wave rectifier, connected to receive the output of the means 38 and rectify the same. The rectified signal is then, in turn, applied to low pass filter 44. The latter is preferably designed to pass the envelope frequencies within the bandwidth of interest. Filter 44 should pass those frequencies below about 10 Hz although this can vary. The output of low pass filter 44 is then applied to threshold detector 46. The latter may also be in the form of a comparator whose threshold is set above ambient noise.

As described in U.S. Pat. No. 4,306,567, each breath takes a finite period of time, for humans typically greater than about 300–900 milliseconds, but not usually exceeding 2-3 seconds. Pulses derived from motion artifacts are typically of a relatively shorter duration, i.e., less than 300–400 milliseconds. Accordingly, means, preferably in the form of pulse discriminator 48, are provided for discriminating between pulses of duration representative of less than a predetermined time period including pulses derived from motion artifacts, e.g., 400 milliseconds, and may also reject those exceeding a predetermined time period, e.g., 3 or 4 seconds. The output of the discriminator 48 is a series or train of pulses, the repetition rate being the sensed respiration rate.

The output of discriminator 48 is applied to the one-shot multivibrator 50, which in turn provides a single pulse of fixed amplitude and a predetermined duration for each pulse received at its input. Thus, each output pulse of multivibrator 50 has a finite amount of energy and is indicative of each respiration cycle. Where the metering of respiration rate is desired, the output of multivibrator 50 can be connected to the input of integrator 52. Since each pulse from multivibrator 50 contains the same amount of signal energy, the integrator will charge and discharge at a rate dependent on the repetition rate of the pulses which is a function of respiration rate. Thus, the voltage level of the output can be applied to a suitable display 54, such as a digital display, to indicate the respiration rate. Similarly, the output of multivibrator 50 can be applied to a light indicator 56 such as an LED (light emitting diode) display so that the latter is energized for each respiration cycle.

The output of multivibrator 50 is also connected so as to provide an apnea monitoring device. More specifically, the output of multivibrator 50 is connected to the input of apnea timer 58. The latter includes integrator 60 connected to the inverting input of threshold amplifier 62. The integrator 58 is set to charge and discharge at rates such that the output of the integrator will fall below the threshold level set at the noninverting input of amplifier 62 when no pulses are received from multivibrator 48 for a predetermined period of time. The output of amplifier 60 then goes to some finite value and drives the alarm 62 giving a sonic or visual indication that the sensor no longer detects respiration.

Various changes can be made to the device of FIG. 1 and the apparatus of FIG. 3 without departing from the principles of the invention. For example, as shown in FIG. 4, the cannula nostril inserts 20A and 20B of the cannula 10A are isolated from one another by placing a closure 70 in the air passageway 14 of the cannula between the two nostril inserts. In this embodiment the end 16A is open so that oxygen can, for example, be administered through the opening and through the one nostril insert 20A. At least a portion of the air flow in response to exhalation will occur through the other insert 20B to the opposite end of the cannula through aperture 26 resulting in resonance occurring in the cavity 24 at the detector 30 as previously described.

It should be appreciated that while the acoustic signal generated in each of the embodiments shown in FIGS. 1, 2 and 4 is of a positive nature, the signal can be diminutive, against a constant source of noise produced, for example, by the constant flow of oxygen. As shown in FIGS. 5 and 6, the nasal cannula has its end 16B connected to a source of oxygen, while the other end 18B is closed. At least one insert prong 80 extends through the wall of the cannula up through one of the nasal inserts 20B and preferably terminates at its end 82 just above the top edge of the insert. The opposite end of the prong 80 is connected to the detector 30. The prong 80 is preferably a hollow tube open at its end 82 and has an internal diameter much smaller than the internal diameter of the insert 20B and passageway 14. As oxygen is supplied to the end 16B and through the passageway, the detector 30 will sense a relatively constant background noise, the characteristics of which are a function of flow rate. When the cannula 10B is placed on the user, in a manner similar to that shown in FIG. 2, the top end 82 of the prong will be disposed in or near a nostril of the user. During inhalation, the oxygen flowing through the cannula passageway will be inhaled by the user. However, during exhalation, physiological air flow will result in a diminution of the oxygen flow through the nasal inserts 20, which results in a diminution of the acoustic signal amplitude so that respiration can be detected and monitored. As will be more evident hereinafter with respect to the description of FIGS. 11 and 16, the signal sensed by detector 30 in the FIG. 5 embodiment can by processed by the Krasner Monitor in a manner hereinafter described with respect to those Figs.

In addition to cannulas, it should be appreciated that the principles of the present invention can be utilized in other devices which define an air passageway which can be connected to carry airflow responsive to respiration. For example, as shown in FIG. 7, the acoustic signal generator means and detector can be connected to an oxygen mask 90. For example, as shown, the front of the mask is typically provided with a connector, generally indicated by numeral 92, for receiving a supply of oxygen. In accordance with the present invention, the mask is modified to include a connector 96 to receive the hollow tube 94, open at its connecting point to the connector 92 of the mask and closed off at its bottom end by a resonant cavity 24, which in turn is connected to the detector 30 for sensing the acoustic signal generated in the resonant cavity. As the user exhales into the mask (the mask defining with the users face the "air passageway") a tuned acoustic signal (whistle) is generated in the hollow tube 94. The detector 30 will sense the acoustic signal in the manner previously described.

Another example of a device which defines an air passageway, which in turn can be connected to carry airflow in response to respiration, is a device which is adapted to be connected between the user and respiration assistance apparatus, such as shown in FIG. 8. Specifically, an adapter 100 is connected between an endotracheal tube 102 and the T-piece connector 104, which in turn connects respiratory tubing to a ventilator 106 (or an anesthesia machine).

Figure 13:
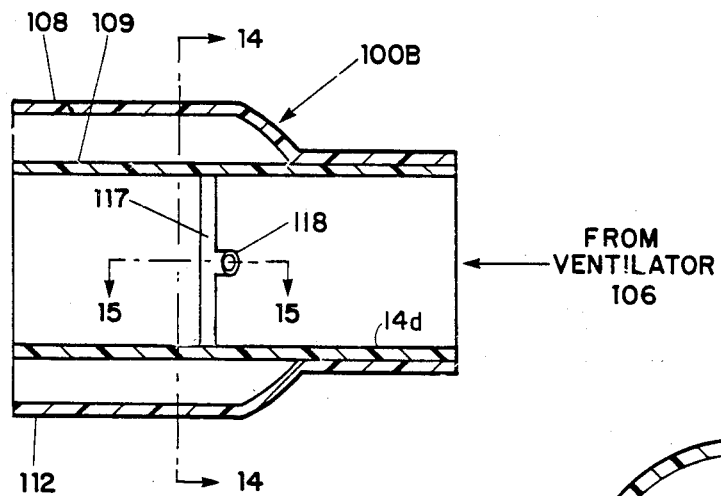
FIG. 13 shows an enlarged perspective axial view of a second embodiment of the acoustic endotracheal tube adapter used in FIG. 8.
Figure 14:
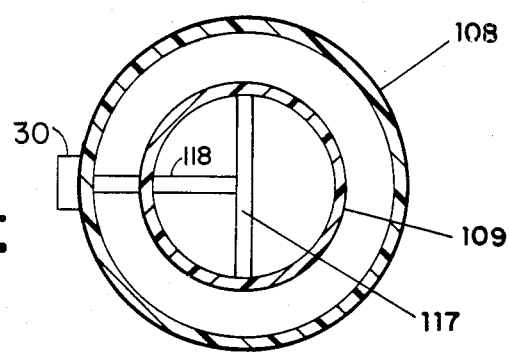
FIG. 14 is a cross-sectional view taken along line 14—14 in FIG. 13.
Figure 15:
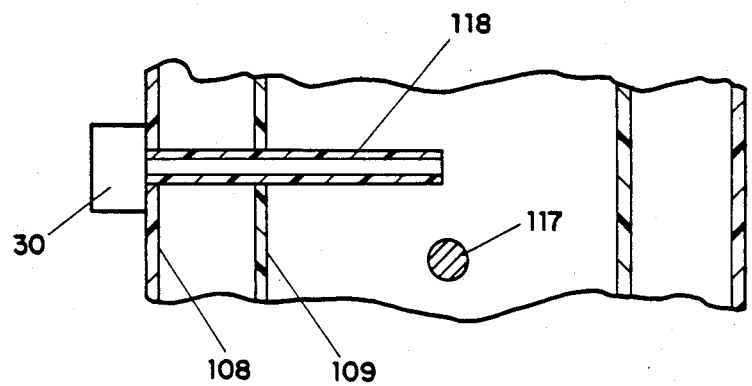
FIG. 15 is a cross-sectional view taken along line 15—15 in FIG. 13.

Embodiments of the adapter 100 are shown in FIGS. 9 and 10 and in FIGS. 13–15.

Referring to FIGS. 9 and 10, the adapter 100A is shown in detail. The adapter shown comprises an outer hollow tube 108 open at opposite ends 110 and 112. The interior of the outer hollow tube defines the passageway 14C of the device. The outer tube 108 is slightly tapered at the end 110 receiving air from the ventilator 106 so as to interface between the T piece connector and the endotracheal tube. A smaller inner hollow tube 114, provided with a flared out opening at one end 116 and attached at its other end to detector 30, has inner and outer cross-sectional dimensions much smaller than those of the passageway. The smaller inner tube preferably extends through the wall of the outer tube and is bent so that the end 116 of the inner tube faces in the direction opposite to the direction of airflow which occurs in response to exhalation by the user (and in the direction of air flow which occurs when air is supplied by the ventilator 106).

As is well-known, the ventilator will assist breathing by forcing air into the lungs of a patient, forcing inhalation, with air being subsequently exhaled from the patient. The ventilator may operate with each breadth of the patient but, more typically, will operate periodically, allowing the patient to breathe in an unassisted manner between each ventilator operation. During the unassisted period, the adapter 100A will generate an acoustic signal with each exhalation. During assisted breathing, however, acoustic (or pressure) signals resulting from airflow from the ventilator (inhalation) and from the user (exhalation) are detected by the detector 30. Both inhalation and exhalation can produce similar acoustic signatures. A typical output signal of the detector (e.g., a microphone) during assisted breathing from the operation of the ventilator behaves in a similar manner shown in FIG. 12. As described in greater detail hereinafter at zero flow the detector output has a bias potential a. During inhalation the bias potential drops to c. After the cessation of inhalation, the bias potential jumps to level e.

Figure 12:
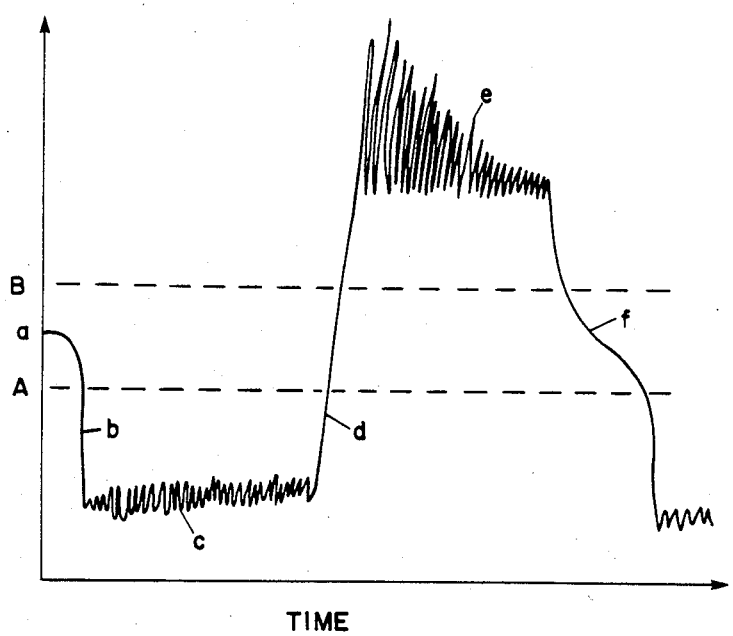
FIG. 12 shows a graph of amplitude vs. time of a typical respiration signal useful in understanding the operation of the FIG. 11 block diagram.

Apparatus for processing the detected signal is shown in FIG. 11. The apparatus of FIG. 11 is a Krasner Monitor modified so as to further enhance the signal to noise ratio of the processed signal by using the signal information at one frequency (in this case the envelope of the signal shown in FIG. 12) to monitor the signal information at another frequency (in this case the signal representive of respiration contained in the envelope). In particular, the detector 30 shown in FIGS. 9 and 10 may be connected in a suitable manner so that its output signal is used to determine the phase (i.e., inhalation or exhalation) of the respiratory cycle. The D.C. operating levels during inhalation (level c) and exhalation (level e) are shown in the example of FIG. 12. The output of detector 30 is connected through its leads to the input amplifier 34 (previously described with respect to FIG. 3). The output of amplifier 34 is connected to the input of a respiration filter 120. The latter is preferaby identical to the type of respiration filter disclosed in U.S. Pat. No. 4,306,567, except that the center frequency is preferably about 200 Hz. Specifically, the respiration filter is preferably a band pass filter having a center frequency or maximum transmission at about 200 Hz. The specific design of the filter may take the form of any one of several types of filters which are known in the art. The filter is preferably of the active type so as to provide a predetermined gain depending upon the relative of the signal. The filter may be a variable state filter with a center frequency of about 200 Hz, and skirts preferably sloping at about 48 dB/octave, although this can vary. The filter is preferably designed to have a Q between about 10 and 100, with 10 being preferred, although the Q can also vary from this value. The output of respiration filter 120 is connected to the input of the means 40 for demodulating the signal output of the filter, as previously described with respect to FIG. 3. The output of demodulator means 40 is connected to the input of gate 122 for selectively transmitting only a predetermined portion of the signal in response to a control signal. The control signal is generated by connecting the output of detector 30 to the input of an automatic threshold detector 124. The latter generally transmits only portions of the signal sensed by the detector 30 which are above a predetermined threshold (shown as level A in FIG. 12 as being slightly below the bias level of the signal) so that substantially all of the portion of the signal associated with inhalation is not transmitted by the threshold detector 124. The output of detector 124 is connected to the input of pulse width discriminator 128 for testing whether the level below the predetermined threshold level A stays below that level by a predetermined period of time (e.g., 0.5–1.0 seconds) so as to insure that inhalation occurred and to establish the expected occurrence of exhalation. This output is connected to the input of a second threshold detector 130. The latter generally transmits only portions of the signal transmitted by the second detector 130 above a predetermined threshold (shown as level B in FIG. 12 as being slightly above the bias level of the signal generated by the detector 30 represented by the sensed respiration signal) so that substantially all of the portion of the signal associated with exhalation is passed by the detector 130. The output of detector 130 is connected to the input of one shot multivibrator 132. The latter provides a pulse of predetermined width in response to each leading edge of the output of detector 130. The output of multivibrator 132 is applied to the control input of gate 122. The latter can be a field effect transistor connected so that its gate electrode receives the control signal from multivibrator 132, which in turn makes the transistor conductive so that it transmits the signal output from the output of demodulator means 40 to the threshold detector 46. The latter is connected to the remainder of the system as shown in FIG. 3.

In operation, the acoustic signal generated in response to respiration is sensed by detector 30, which in turn provides an output signal similar to the one shown in FIG. 12. At very low frequencies (i.e., typical frequencies associated with normal respiration rates such as those between 0.1 Hz to 1.0 Hz) the output of the detector 30 of the FIGS. 9 and 10 adapter behaves similar to a pressure detector although not identical. The detector 30 generates the waveforms of FIG. 12 in response to each respiratory cycle. During inspiratory flow the bias level drops as is shown at b, while c indicates the duration of inhalation. When inspiratory flow ceases the bias level rapidly rises to a higher level e, the positive slope transition being indicated by d. After the positive transition d, the higher frequencies of expiratory flow are shown at e superimposed on the new biased level. At the end of exhalation indicated at f, the cycle repeats itself. This signal is transmitted to the amplifier 34. The amplified output of amplifier 34 is filtered by respiration filter 120 before being applied to the demodulating means 40. The output of means 40 is essentially the envelope of the signal shown in FIG. 12. The signal output of detector 30 is also applied to the automatic threshold detector 124 which senses that portion of the signal below the threshold level A. The remaining portion of the signal, above threshold level A, is transmitted to the discriminator 128. The latter tests whether the level of the signal below threshold level A is for a predetermined period of time, so as to insure that the inspiratory portion of the cycle has occurred. If so, the remaining portion of the signal is transmitted to the second threshold detector 130 set to transmit those portions of the signal above threshold level B. The leading edge of this portion of the signal (part d of the signal above level B) will trigger one shot multivibrator 132. The latter provides a pulse for a predetermined duration providing a window for a portion of the expiratory portion of the signal. The 200 Hz center frequency of the respiration filter represents the near-optimum signal-to-noise ratio associated with a ventilator-patient connection, and is outside of the resonant frequency of the respiratory tubing. The problem with using a single bandpass is that it might prove difficult to distinguish between inhalation and exhalation. By requiring the time measurement and elimination of the inspiration portion of the respiration cycle before measuring the exhalation portion of the respiration cycle, the system ignores all signals until inhalation has been completed and exhalation has commenced. Since the time for the expected onset of exhalation is precisely known, i.e., at the end of inhalation, the requirement established in U.S. Pat. No. 4,306,567 for optimum signal-to-noise is enhanced by only looking at the expiratory portion of the cycle through a precise time window. By using the system of FIG. 11 the signal information carried by the envelope of the signal shown in FIG. 12 is used to distinguish between inhalation and exhalation. As described, by sensing exhalation, if the endotracheal tube 102 of FIG. 8 becomes extubated from the patient, airflow indicating inhalation (from the ventilator) will continue but airflow indicating exhalation will cease. However, since only airflow in response to exhalation is being used to monitor respiration, the system will sense the disconnection of the endotracheal tube.

Referring to FIGS. 13–15, the alternative adapter 100B includes the outer tube 108 which is substantially identical to that shown in the adapter of FIGS. 9 and 10, and an inner hollow cylindrical tube 109 coaxially mounted in the outer tube and defining the air passageway 14D. A vortex shedding element 117, preferably in the form of a cylindrical pin, is connected diametrically across the center interior portion of the inner tube 109. A thin hollow tube 118 extends through the outer tube 108 and the inner tube 109. Tube 118 has an open end positioned just downstream (with respect to airflow in direction from the user during exhalation) and its other end connected to the detector 30. Generally, air flowing in response to exhalation will be substantially laminar in the inner tube 109 until it strikes the vortex shedding element whereupon vortices are created downstream from the element 117. Such vortices will create an acoustic signal which is sensed by detector 30. With the detector 30 positioned upstream with respect to airflow from the ventilator and downstream with respect to airflow in response to exhalation the output signal of detector 30 will be similar to that obtained from the resonant cavity 24 of the previously described embodiments employing the cavity. Thus, the apparatus of FIG. 3 can be used to process the output signal of the detector 30 in the adapter shown in FIGS. 13–15.

It should be appreciated that the respiration signal can be processed by monitors of the Krasner type, other than those shown in FIGS. 3 and 11, without departing from the scope of the invention. For example, the techniques shown in FIGS. 3 and 11 have been combined in the system shown in FIG. 16. As shown, the output of detector 30 is connected to the input of amplifier 34. The latter has its output connected to the gate 122. The output of detector 30 is connected to the automatic threshold detector 124, which in turn has its output connected to the input of pulse width discriminator 128. The latter has its output connected to the input of the second threshold detector 130. Detector 130 has its output connected to the input of one shot multivibrator 132, which in turn has its output connected to control the conduction of the gate 122. The output of gate 122 is connected to the input of band pass filter 36, which in turn is connected to the means 38 for locking onto the tuned frequency signal. The output of means 38 is connected to the demodulator means 40, with the remainder of the circuit identical to that shown in FIG. 3.

Figure 16:
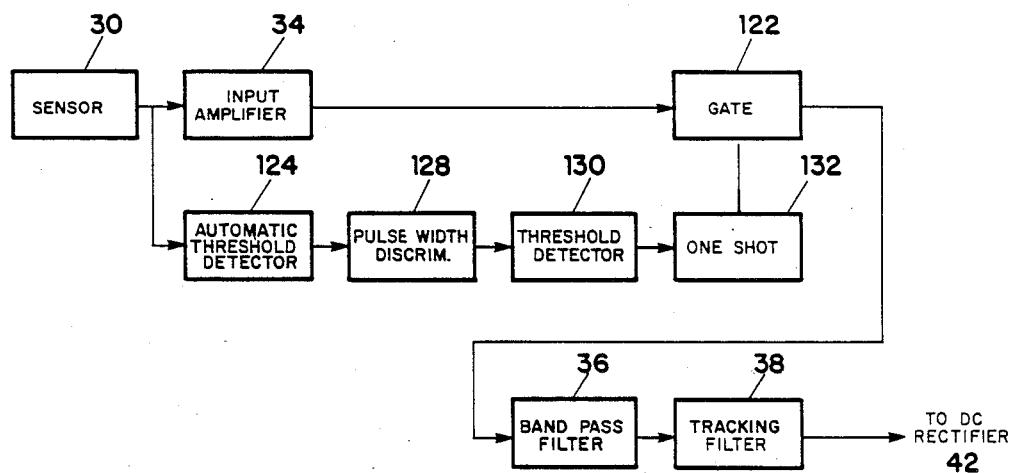
FIG. 16 is a block diagram of yet another embodiment of the Krasner Monitor which has been modified to incorporate the present invention.

In operation, detector 124, pulse width discriminator 128, detector 130 and multivibrator 132 provide the control gating signal, as in the FIG. 11 system so that a window is provided during exhalation. This portion is filtered by filter 36 and tracked by the means 38, as described with respect to FIG. 3. Thus, the system of FIG. 16 combines the techniques of both FIGS. 3 and 11. Further, where the nature of the signal of FIG. 12 is opposite, (i.e., the portion c represents exhalation and portion e represents inhalation, as might be generated by the cannula of FIG. 5) the output of the detector 30 can be inverted. Similar signal processing would produce the desired result. Another modification which can be made to the systems shown in FIGS. 11 and 16, is that a derivative circuit for providing an output signal for positive going signals, i.e., portion d of the signal shown in FIG. 12, can be substituted for the threshold detector 124.

The invention therefore provides a useful way of acquiring a physiological signal, such as that associated with respiration. The device is simple and relatively inexpensive to manufacture. The particular acoustic frequency of interest or bandpass of acoustic frequencies is selected according to the requirements of the physiological signal and the environment from which it must be selected. In this way the precise frequency at which the Krasner Monitor is operated can be selected to optimize, as well as further enhance the signal-to-noise ratio.

Since certain changes may be made in the above apparatus without departing from the scope of the invention herein involved, it is intended that all of the matter contained in the above description and the accompanying drawings shall be interpreted in an illustrative and not in a limiting sense.

What is claimed is:

1. A device for sensing respiration in a living body, said device comprising
   means adapted to be positioned relative to the respiratory airway of said living body so as to define an air passageway for providing airflow in a first direction responsively to inhalation by said body and a second direction responsively to exhalation by said body;
   acoustic signal generating means disposed relative to said passageway for generating a distinctive acoustic signal responsively to airflow from said body in only a selected one of said first and second directions, said acoustic signal having a fundamental frequency higher than the dominant acoustic frequencies normally present in the natural acoustic signals generated by said body during respiration; and
   means disposed relative to said acoustic signal generating means for detecting said acoustic signal and for generating an electrical signal representative of said acoustic signal.

2. A device according to claim 1 wherein said acoustic signal generating means includes a resonant cavity disposed relative to said air passageway so that only air flowing in said one of said first and second directions generates said distinctive acoustic signal in said resonant cavity.

3. A device according to claim 2, wherein said means defining said air passageway includes a nasal cannula and said resonant cavity is attached to said cannula.

4. A device according to claim 3, wherein said cannula includes a pair of nasal inserts in fluid communication with said air passageway for insertion in the nasal orifices of the living body and said resonant cavity is positioned at one end of said cannula.

5. A device according to claim 4, wherein said resonant cavity is a closed ended cavity provided at one end of said cannula, the end of said cannula oppsite said cavity is closed and said inserts are disposed between said ends.

6. A device according to claim 5, wherein said nasal inserts are axially displaced from another between said ends of said cannula, and said cannula further includes an air obstruction in said passageway between said inserts.

7. A device according to claim 4, wherein said resonant cavity is a whistle.

8. A device according to claim 1, wherein said device is adapted to be used with apparatus generating a source of acoustic noise including noise at said fundamental frequency in response to the flow of air from said apparatus in the other of said first and second directions and wherein said means for detecting said acoustic signal generates said electrical signal representative of said acoustic signal and said acoustic noise such that said electrical signal diminishes in amplitude in response to air flow in said other of said first and second directions.

9. A device according to claim 1, wherein said means disposed relative to said passageway includes at least one prong disposed in said passageway having a cross-sectional diameter substantially smaller than the internal cross-sectional dimensions of said passageway.

10. A device according to claim 1, wherein said acoustic signal generating means includes a tubular body having an open end and being of smaller cross-sectional dimensions than said passageway, said tubular body extending into said passageway with said open end positioned to receive air flowing in said passageway in said one direction.

11. A device according to claim 10, wherein the end of said tubular body opposite said open end is secured to said means for detecting said acoustic signal and for generating said electrical signal.

12. A device according to claim 1, wherein said acoustic signal generating means includes a vortex shedding element for generating air current eddies in said passageway in response to airflow in at least said one direction, and said means for detecting said acoustic signal is positioned downstream relative to said vortex shedding element in the direction of air flow in said one direction.

13. A device according to claim 1, further including a mask adapted to be worn by said living body and defining in part said passageway, and wherein said acoustic signal generating means and said means for detecting said acoustic signal are attached to said mask.

14. A device according to claim 1, wherein said acoustic signal generating means generates said distinctive acoustic signal in response to exhalation from said body.

15. In a system for sensing the respiration function of a subject, said system comprising, in combination: (a) detection means for detecting select acoustic energy generated in response to the respiration function of said subject; (b) signal generating means for generating an electrical signal within a predetermined range of frequencies and representative of said acoustic energy generated in response to the respiration function of said subject and detected by said detection means within said range; and (c) demodulation means for demodulating said electrical signal so as to produce a demodulated electrical signal and so as to detect a periodic amplitude modulation frequency of the electrical signal; wherein said system further comprises:

means adapted to be positioned relative to the respiratory airway of said subject so as to define an air passageway for providing airflow in a first direction responsively to inhalation by said subject and a second direction responsively to exhalation by said subject; and acoustic signal generating means disposed relative to said passageway for generating a distinctive acoustic signal including said select acoustic energy responsively to airflow from said body in only a selected one of said first and second directions, said acoustic signal having a fundamental frequency higher than the dominant acoustic frequencies normally present in the natural acoustic signals generated by said body during respiration;

wherein said detection means is disposed relative to said acoustic signal generating means for detecting said acoustic signal and for generating said electrical signal representative of said acoustic signal.

16. A system according to claim 15, wherein said acoustic signal generating means includes a resonant cavity disposed relative to said air passageway so that only air flowing in said one of said first and second directions generates said acoustic signal in said resonant cavity.

17. A system according to claim 16, wherein said means adapted to be positioned relative to the respiratory airway and defining said air passageway includes a nasal cannula and said resonant cavity is attached to said cannula.

18. A system according to claim 17, wherein said cannula includes a pair of nasal inserts in fluid communication with said air passageway for insertion in the nasal orifices of the living body and said resonant cavity is positioned at one end of said cannula.

19. A system according to claim 18, wherein said resonant cavity is a closed ended cavity provided at one end of said cannula, the end of said cannula opposite said cavity is closed and said inserts are disposed between said ends.

20. A system according to claim 19, wherein said nasal inserts are axially displaced from one another between said ends of said cannula, and said cannula further includes an air obstruction in said passageway between said inserts.

21. A system according to claim 18, wherein said resonant cavity is a whistle.

22. A system according to claim 15, wherein said system is adapted to be used with apparatus generating a source of acoustic noise including noise at said fundamental frequency in response to the flow of air from said apparatus in the other of said first and second directions, and wherein said means for detecting said acoustic signal generates said electrical signal representative of said acoustic signal and said acoustic noise such that said electrical signal diminishes in amplitude in response to airflow in said other of said first and second directions.

23. A system according to claim 22, said system further including means responsive to said electrical signal generated by said detector means for distinguishing between those portions of the electrical signal which are representative of airflow in said one of said first and second directions and those portions of the signal which are representative of airflow in the other of said first and second directions and means for generating a second electrical signal representative of only those portions of the first-mentioned electrical signal representative of airflow in said one of said first and second directions.

24. A system according to claim 23, wherein said means for distinguishing between said portions of said first-mentioned electrical signal includes a threshold detector.

25. A system according to claim 15, wherein said means disposed relative to said passageway includes at least one prong disposed in said passageway and having a cross-sectional diameter substantially smaller than the internal cross-sectional dimensions of said passageway.

26. A system according to claim 15, wherein said acoustic signal generating means includes a tubular body having an open end and being of smaller cross-sectional dimensions than said passageway, said tubular body extending into said passageway with said open end positioned to receive air flowing in said passageway in said one direction.

27. A system according to claim 26, wherein the end of said tubular body opposite said open end is secured to said means for detecting said acoustic signal and for generating said electrical signal.

28. A system according to claim 15, wherein said acoustic signal generating means includes a vortex shedding element for generating air current vortices in said passageway in response to airflow in at least said one direction, and said means for detecting said acoustic signal is positioned downstream relative to said vortex shedding element in the direction of airflow in said one direction.

29. A system according to claim 15, further including a mask adapted to be worn by said living body and defining in part said passageway, and wherein said acoustic signal generating means and said means for detecting said acoustic signal are attached to said mask.

30. A system according to claim 15, wherein said acoustic signal generating means generates said distinctive acoustic signal in response to exhalation from said body.

31. A system for monitoring a physiological repetitive function of a subject, said system comprising, in combination:

detection means for detecting acoustic energy generated in response to the physiological repetitive function of said subject;

signal generating means responsive to the acoustic energy detected by said detection means for generating a first electrical signal containing signal information within at least two bands of frequencies of said detected acoustic energy; and means responsive to the signal information in one of said hands for generating a second electrical signal as a function of only preselected portions of said signal information in the other of said bands; and means for processing said second electrical signal so as to produce a third signal representative of said physiological repetitive function.

32. A system according to claim 31, wherein said first electrical signal contains said signal information withing two corresponding bands of electrical frequencies, said one band of frequencies of said first electrical signal contains the envelope frequency of said detected acoustic energy and said other band of frequencies of said first electrical signal contains a frequency representative of the natural frequency of and physiological function, and said means for generating said second electrical signal includes means for detecting a predetermined portion of the envelope of said first electrical signal so as to sense the signal information within said other band of said first electrical signal only within preselected portions of said envelope of said first electrical signal.

33. A system according to claim 32, wherein said means for detecting said predetermined portion of said envelope includes means for generating a control signal as a function of a first predetermined phase of each cycle of said envelope, and said means for detecting a predetermined portion of said envelope of said first electrical signal senses the signal information within said other band only within a second predetermined phase.

34. A system according to claim 33, wherein said physiological function is respiration, said means for generating said control signal generates said control signal as a function of a phase of each cycle of said envelope occurring substantially during inhalation and said means for detecting said predetermined portion of said envelope of said first electrical signal detects the signal information within the other band within a phase of each cycle occurring substantially during exhalation.

35. A device for sensing respiration in a living body, said device comprising:
    means adapted to be positioned relative to the respiratory airway of said living body so as to define an air passageway for providing airflow in a first direction responsively to inhalation by said body and a second direction responsively to exhalation by said body;
    acoustic signal generating means disposed relative to said passageway for generating a distinctive acoustic signal responsively to airflow from said body in only a selected one of said first and second directions; and
    means disposed relative to said acoustic signal generating means for detecting said acoustic signal and for generating an electrical signal representative of said acoustic signal.

36. A device according to claim 35, wherein said acoustic signal generating means includes a resonant cavity disposed relative to said air passageway so that only air flowing in said one of said first and second directions generates said distinctive acoustic signal in said resonant cavity.

37. A device according to claim 36, wherein said means defining said air passageway includes a nasal cannula and said resonant cavity is attached to said cannula.

38. A device according to claim 37, wherein said cannula includes a pair of nasal inserts in fluid communication with said air passageway for insertion in the nasal orifices of the living body and said resonant cavity is positioned at one end of said cannula.

39. A device according to claim 38, wherein said resonant cavity is a closed ended cavity provided at one end of said cannula, the end of said cannula opposite said cavity is closed and said inserts are disposed between said ends.

40. A device according to claim 39, wherein said nasal inserts are axially displaced from one another between said ends of said cannula, and said cannula further includes an air obstruction in said passageway between said inserts.

41. A device according to claim 38, wherein said resonant cavity is a whistle.

42. A device according to claim 35, wherein said means disposed relative to said passageway includes at least one prong disposed in said passageway having a cross-sectional diameter substantially smaller than the internal cross-sectional dimensions of said passageway.

43. A device according to claim 35, wherein said acoustic signal generating means includes a tubular body having an open end and being of smaller cross-sectional dimensions than said passageway, said tubular body extending into said passageway with said open end positioned to receive air flowing in said passageway in said one direction.

44. A device according to claim 43, wherein the end of said tubular body opposite said open end is secured to said means for detecting said acoustic signal and for generating said electrical signal.

45. A device according to claim 35, wherein said acoustic signal generating means includes a vortex shedding element for generating air current eddies in said passageway in response to airflow in at least said one direction, and said means for detecting said acoustic signal is positioned downstream relative to said vortex shedding element in the direction of airflow in said one direction.

46. A device according to claim 35, further including a mask adapted to be worn by said living body and defining in part said passageway, and wherein said acoustic signal generating means and said means for detecting said acoustic signal are attached to said mask.

47. A device according to claim 35, wherein said acoustic signal generating means generates said distinctive acoustic signal in response to exhalation from said body.

48. In a system for sensing the respiration function of a subject, said system comprising, in combination: (a) detection means for detecting select acoustic energy generated in response to the respiration function of said subject; (b) signal generating means for generating an electrical signal within a predetermined range of frequencies and representative of said acoustic energy generated in response to the respiration function of said subject and detected by said detection means within said range; and (c) demodulation means for demodulating said electrical signal so as to produce a demodulated electrical signal and so as to detect a periodic amplitude modulation frequency of the electrical signal; wherein said system further comprises:
    means adapted to be positioned relative to the respiratory airway of said subject so as to define an air passageway for providing airflow in a first direction responsively to inhalation by said subject and a second direction responsively to exhalation by said subject; and
    acoustic signal generating means disposed relative to said passageway for generating a distinctive acoustic signal including said select acoustic energy responsively to airflow from said body in only a selected one of said first and second directions;
    wherein said detection means is disposed relative to said acoustic signal generating means for detecting said acoustic signal and for generating said electrical signal representative of said acoustic signal.

49. A system according to claim 48, wherein said acoustic signal generating means includes a resonant cavity disposed relative to said air passageway so that only air flowing in said one of said first and second directions generates said acoustic signal in said resonant cavity.

50. A system according to claim 49, wherein said means adapted to be positioned relative to the respiratory airway and defining said air passageway includes a nasal cannula and said resonant cavity is attached to said cannula.

51. A system according to claim 50, wherein said cannula includes a pair of nasal inserts in fluid communication with said air passageway for insertion in the nasal orifices of the living body and said resonant cavity is positioned at one end of said cannula.

52. A system according to claim 51, wherein said resonant cavity is a closed ended cavity provided at one end of said cannula, the end of said cannula opposite said cavity is closed and said inserts are disposed between said ends.

53. A system according to claim 52, wherein said nasal inserts are axially displaced from one another between said ends of said cannula, and said cannula further includes an air obstruction in said passageway between said inserts.

54. A system according to claim 51, wherein said resonant cavity is a whistle.

55. A system according to claim 48, wherein said means disposed relative to said passageway includes at least one prong disposed in said passageway and having a cross-sectional diameter substantially smaller than the internal cross-sectional dimensions of said passageway.

56. A system according to claim 48, wherein said acoustic signal generating means includes a tubular body having an open end and being of smaller cross-sectional dimensions than said passageway, said tubular body extending into said passageway with said open end positioned to receive air flowing in said passageway in said one direction.

57. A system according to claim 56, wherein the end of said tubular body opposite said open end is secured to said means for detecting said acoustic signal and for generating said electrical signal.

58. A system according to claim 48, wherein said acoustic signal generating means includes a vortex shedding element for generating air current vortices in said passageway in response to airflow in at least said one direction, and said means for detecting said acoustic signal is positioned downstream relative to said vortex shedding element in the direction of airflow in said one direction.

59. A system according to claim 48, further including a mask adapted to be worn by said living body and defining in part said passageway, and wherein said acoustic signal generating means and said means for detecting said acoustic signal are attached to said mask.

60. A system according to claim 48, wherein said acoustic signal generating means generates said distinctive acoustic signal in response to exhalation from said body.

* * * * *